(12) United States Patent
Burckhardt et al.

(10) Patent No.: US 9,394,230 B2
(45) Date of Patent: Jul. 19, 2016

(54) HARDENERS FOR EPOXY RESIN COATINGS

(71) Applicant: SIKA TECHNOLOGY AG, Baar (CH)

(72) Inventors: Urs Burckhardt, Zürich (CH); Edis Kasemi, Zürich (CH)

(73) Assignee: SIKA TECHNOLOGY AG, Baar (CH)

( * ) Notice: Subject to any disclaimer, the term of this patent is extended or adjusted under 35 U.S.C. 154(b) by 110 days.

(21) Appl. No.: 14/357,461

(22) PCT Filed: Nov. 8, 2012

(86) PCT No.: PCT/EP2012/072193
§ 371 (c)(1),
(2) Date: May 9, 2014

(87) PCT Pub. No.: WO2013/068502
PCT Pub. Date: May 16, 2013

(65) Prior Publication Data
US 2014/0288247 A1  Sep. 25, 2014

(30) Foreign Application Priority Data
Nov. 10, 2011 (EP) .................................. 11188693

(51) Int. Cl.
*C08G 59/50* (2006.01)
*C07C 211/49* (2006.01)
*C08G 59/18* (2006.01)
*C08L 63/00* (2006.01)

(52) U.S. Cl.
CPC ............ *C07C 211/49* (2013.01); *C08G 59/184* (2013.01); *C08G 59/504* (2013.01); *C08G 59/5033* (2013.01); *C08L 63/00* (2013.01)

(58) Field of Classification Search
None
See application file for complete search history.

(56) References Cited

U.S. PATENT DOCUMENTS

| 3,574,221 A | 4/1971 | Hankovszky et al. |
| 4,120,913 A | 10/1978 | Petrie |
| 4,978,792 A | 12/1990 | Nagata et al. |
| 2009/0163676 A1 | 6/2009 | Vedage et al. |
| 2014/0275446 A1* | 9/2014 | Kramer ............ C08G 59/5033 525/523 |

FOREIGN PATENT DOCUMENTS

CH  WO 2013/068507 A1 *  5/2013  ........... C08G 59/182

OTHER PUBLICATIONS

HCAPLUS accession No. 2013:759655 for European Patent No. 259,101 A1 and U.S. Publication No. 2014/0288247 of U.S. Appl. No. 14/357,461, May 15, 2013, two pages.*
International Preliminary Report on Patentability issued in PCT/EP2012/072193 on May 13, 2014.
International Search Report issued in International Application No. PCT/EP2012/072193 dated Jul. 11, 2013 (with translation).
Oct. 14, 2015 Office Action issued in Chinese Patent Application No. 201280048100.0.

* cited by examiner

*Primary Examiner* — Robert Sellers
(74) *Attorney, Agent, or Firm* — Oliff PLC

(57) ABSTRACT

The invention relates to hardeners for epoxy resin containing secondary amino groups having dialkyl amino phenyl groups. The hardeners have a surprisingly low viscosity and harden surprisingly fast together with the epoxy resins, even in moist, cold conditions, and without blushing to form films with high hardness and stability. They are suitable, in particular, for low-emission coatings.

13 Claims, No Drawings

HARDENERS FOR EPOXY RESIN COATINGS

TECHNICAL FIELD

The invention relates to the area of amines as hardeners for epoxy resins and amine-containing epoxy resin compositions and the use thereof, especially as coatings.

PRIOR ART

Epoxy resin compositions should exhibit a number of properties to be useful as high-quality coatings. On one hand they should have a low viscosity so that they are readily processable at ambient temperature and self-leveling, and they should rapidly undergo hardening without so-called blushing effects, even under moist, cold conditions. "Blushing" means the development of defects during hardening, such as cloudiness, spots and rough or sticky surfaces caused by salt formation of amines with atmospheric carbon dioxide ($CO_2$), wherein high atmospheric humidity and low temperatures promote the occurrence of blushing effects. In the fully hardened state, the epoxy resin coating should have a level surface without clouding, spots or craters, and it should have high hardness and good stability. To achieve these properties, diluents are usually used in epoxy resin coatings according to the prior art. Such diluents, for example benzyl alcohol or phenols, are not incorporated into the resin matrix during the hardening. Today, however, there is increasing demand for low-emission systems, which have a low content of substances that fan be released by evaporation or diffusion processes after the hardening. Therefore, only small amounts of substances that can be released by processes of evaporation or diffusion, or none at all can be used in low-emission systems.

US 2009/0163676 describes hardener compositions containing one or more benzylated polyalkylene polyamines and one or more additional amines. Without adducting with epoxides, these hardeners only harden very slowly with epoxy resins, especially in a cold environment. To be sure, partial adducting on epoxides results in faster hardening, but the viscosity of the hardeners is greatly increased in the process.

PRESENTATION OF THE INVENTION

The goal of the present invention is therefore that of supplying a hardener for epoxy resins that is of low viscosity, can be processed well together with epoxy resins, and can undergo hardening even under cold, moist conditions fast and without blushing effects to form coatings of high hardness and stability.

Surprisingly it was found that hardeners according to claim 1 containing amines with at least one amino group of formula (I) solve this problem. The hardeners according to claim 1 are low-odor and highly compatible with epoxy resins. Their viscosity is surprisingly low, especially compared with other amines which instead of the tertiary amino group contain another phenyl ring-activating group, for example a hydroxyl group (phenol group). These hardeners have surprisingly little color, despite the easy discoloration ability of the initial compounds. They harden surprisingly fast with epoxy resins, in particular even under cold, moist conditions, producing coatings with an astonishingly low discoloration tendency.

Additional aspects of the invention form the subject matter of additional independent claims. Particularly preferred embodiments of the invention are the subject matter of the dependent claims.

Methods for Implementing the Invention

The subject matter of the invention is a hardener suitable for hardening epoxy resins, containing one or more amines with one or more amino groups of formula (I),

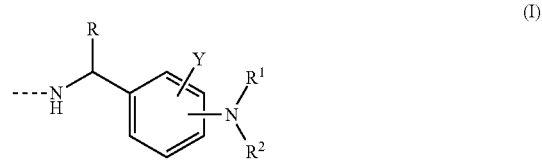

(I)

wherein

R represents a hydrogen atom or an alkyl group with 1 to 12 C atoms, preferably a hydrogen atom or a methyl group, especially a hydrogen atom;

$R^1$ and $R^2$ each independently represent an alkyl or arylalkyl group with 1 to 12 C atoms, or together represent an alkylene group with 4 to 5 C atoms, preferably at least one alkyl group with 1 to 4 C atoms, especially a methyl group; and Y represents a hydrogen atom or an alkyl or alkoxy group with 1 to 12 C atoms, preferably a hydrogen atom or a methyl group, especially a hydrogen atom.

The broken lines in the formulas in this document in each case represent the bond between a substituent and the corresponding remainder of the molecule.

Substance names beginning with "poly," such as polyamine, polyol or polyepoxide, refer to substances which formally contain two or more of the functional groups appearing in their name per molecule.

The term "aliphatic" refers to an amine, the amino group of which is bound to an aliphatic, cycloaliphatic or arylaliphatic radical; correspondingly this group is designated as an aliphatic amino group.

The term "aromatic" refers to an amine, the amino group of which is bound to an aromatic radical; correspondingly, this group is designated as an aromatic amino group.

The term "amine hydrogen" refers to the hydrogen atoms of primary and secondary amino groups.

The term "non-incorporable diluents" refers to a substance soluble in an epoxy resin and reducing its viscosity which is not incorporated covalently into the resin matrix during the hardening of the epoxy resin.

The term "viscosity" in the present document refers to the dynamic viscosity or shear viscosity, which is defined by the ratio between the shear stress and the shear rate (velocity gradient) and is determined as described in accordance with DIN EN ISO 3219.

Preferably the amine with one or more amino groups of formula (I) one, two or three, particularly preferably one or two, amino groups of formula (I). These amines are of particularly low viscosity.

An amine with only one amino group of formula (I) preferably additionally has at least one additional group reactive toward epoxy groups, especially one additional secondary amino group. Particularly preferably the additional secondary amino group has a benzyl radical or a hydroxybenzyl radical. In this way it is possible to modify properties of the amine such as viscosity or reactivity with epoxy groups.

Preferably the amine with one or more amino groups of formula (I) has no primary amino groups. Such amines are particularly suitable as hardeners for epoxy resins, since no blushing effects occur during hardening.

The dialkylamino group preferably occupies the para-position relative to the amino group of formula (I).

Preferably Y represents a hydrogen atom, $R^1$ and $R^2$ each represent a methyl group, and the tertiary amino group is in para-position. One such amino group of formula (I) is an amino group of formula (I a).

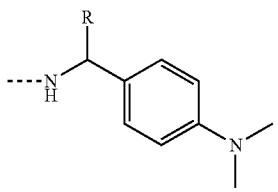
(Ia)

In formula (I a), R has the significance previously mentioned. Amines with amino groups of formula (I a) have particularly low viscosities.

The amine with one or more amino groups of formula (I) is preferably either an amine of formula (II),

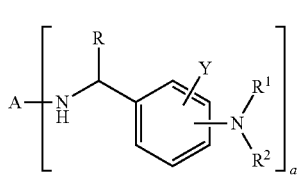
(II)

wherein

A represents an a-valent hydrocarbon radical with a molecular weight in the range of 28 to 5000 g/mol, which optionally has ether groups, amino groups, hydroxyl groups or mercapto groups;

a represents an integer of 1 to 3, preferably 1 or 2; and

R, $R^1$, $R^2$ and Y have the aforementioned meanings;

or it represents an adduct of an amine of formula (II) with one or more compounds containing at least one, preferably at least two, reactive groups, the same or different, selected from the group consisting of epoxide, episulfide, aziridine, cyclocarbonate, isocyanate, isothiocyanate, acryloyl, methacryloyl and acrylamide groups.

Preferably A represents an a-valent hydrocarbon radical with a molecular weight in the range of 28 to 500 g/mol, which optionally contains ether groups or primary or secondary amino groups.

Particularly preferably, A represents either
  an a-valent alkyl, cycloalkyl or arylalkyl radical with 2 to 20, especially 2 to 12, C atoms; or
  an a-valent polyalkyleneamine radical with 1 to 10, especially 1 to 7, secondary amino groups, wherein especially ethylene, n-propylene or hexamethylene is present as the alkylene; or
  an a-valent polyoxyalkylene radical with 1 to 7 ether groups, especially ethylene or isopropylene are present as wherein as the alkylene;
wherein these radicals may have one or two, preferably one, primary or secondary aliphatic amino groups.

In particular, A represents the a-valent hydrocarbon radical of an amine after removal of one primary aliphatic amino group, wherein the amine is selected from the group consisting of 1,5-diamino-2-methylpentane (MPMD), 2-butyl-2-ethyl-1,5-pentanediamine (C11-neodiamine), 1,6-hexanediamine, 2,5-dimethyl-1,6-hexanediamine, 2,2,4- and 2,4,4-trimethylhexamethylenediamine (TMD), 1,12-dodecanediamine, 1,4-diaminocyclohexane, bis-(4-aminocyclohexyl)-methane, bis-(4-amino-3-methylcyclohexyl)methane, 1-amino-3-aminomethyl-3,5,5-trimethylcyclohexane (=isophorone diamine or IPDA), 1,3-bis-(aminomethyl)-cyclohexane, 2,5(2,6)-bis-(aminomethyl)bicyclo[2.2.1]heptane (NBDA), 3(4),8(9)-bis-(aminomethyl)-tricyclo[5.2.1.0$^{2,6}$]decane, 1,3-bis-(aminomethyl)benzene, bis-hexamethylenetriamine (BHMT), diethylenetriamine (DETA), triethylenetetramine (TETA), tetraethylenepentamine (TEPA), pentaethylenehexamine (PEHA), polyethylenepolyamine with 5 to 7 ethyleneamine units (so-called "higher ethylenepolyamines", HEPA), dipropylenetriamine (DPTA), N-(2-aminoethyl)-1,3-propanediamine (N3-amines), N,N'-bis(3-aminopropyl)ethylenediamine (N4-amines) and polyoxyalkylene-diamines and polyoxyalkylene triamines with a molecular weight of 200 to 500 g/mol.

Amines of formula (II) with the preferred hydrocarbon radicals A are particularly compatible with epoxy resins and harden quickly without blushing effects to form high-quality films.

In a very particularly preferred embodiment, A represents the hydrocarbon radical of MPMD or 1,6-hexanediamine or TMD or 1,3-bis-(aminomethyl)benzene or 1,3-bis-(aminomethyl)cyclohexane or bis-(4-aminocyclohexyl)-methane or isophorone diamine after removal of the primary amino groups. Amines of formula (II) with these radicals A give high hardness and stability upon hardening with epoxy resins.

In a further very particularly preferred embodiment, A represents the hydrocarbon radical of DETA, TETA, TEPA, PEHA, HEPA, DPTA, N3-amine or N4-amine after removal of the primary amino groups. Amines of formula (II) with these radicals A upon hardening with epoxy resins give particularly high crosslinking densities and particularly high hardness and stability.

In a further highly particularly preferred embodiment, A represents the hydrocarbon radical of a polyoxyalkylene diamine or polyoxyalkylene triamine with a molecular weight of 200 to 500 g/mol after removal of the primary amino groups. Amines of formula (II) with these radicals A upon hardening with epoxy resins give particularly high impact strengths.

In one embodiment of the invention, the amine with one or more amino groups of formula (I) represents an adduct of an amine of formula (II) with one or more compounds with the previously mentioned reactive groups. For this purpose, the amino groups are used in stoichiometric excess relative to the previously mentioned reactive groups, especially in the range of 2 to 10 amino groups pro previously mentioned reactive group. In this way, adducts with one or more amino groups of formula (I) can be obtained. If the amine of formula (II) used for adducting contains primary amino groups, these preferably react with the aforementioned reactive groups.

Such adducts are produced under known conditions, such as those that are typical for reactions between the reaction groups involved. The preparation is performed using a solvent or preferably without a solvent. Optionally, auxiliary materials such as catalysts, initiators or stabilizers may also be used.

Particularly suitable compounds with the reactive groups mentioned are:
  mono- or polyepoxides, especially epoxy resins or reactive diluents for epoxy resins, which are described in the following as constituents of an epoxy resin composition, as well as methylglycidyl ethers, ethylglycidyl ethers and propylglycidyl ethers;

monomeric and oligomeric polyisocyanates, as well as reaction products of polyisocyanates containing more than one isocyanate group with polyols;

compounds having more than one acrylic, methacrylic or acrylamide group such as tris-(2-hydroxyethyl)-isocyanurate-tri(meth)acrylate, tris-(2-hydroxyethyl)-cyanurate-tri(meth)acrylate, N,N',N''-tris-(meth)acryloyl-perhydrotriazine; acrylates and methacrylates of aliphatic polyethers, polyesters, Novolacs, phenols, aliphatic or cycloaliphatic alcohols, glycols and polyester glycols as well as mono- and polyalkoxylated derivatives of the aforementioned compounds, adducts of polyepoxides with acrylic and methacrylic acid, polyurethane(meth) acrylates and acrylamides such as N,N'-methylene-bis-acrylamide;

and heterofunctional compounds, in other words, compounds containing at least two different ones of the aforementioned reactive groups.

In a preferred embodiment, the adduct is an adduct of an amine of formula (II) with at least one mono- or polyepoxide, especially with at least one mono- or diepoxide.

Preferably the amine with one or more amino groups of formula (I) is an amine of formula (II). An amine of formula (II) has a particularly low viscosity.

Preferably the amine of formula (II) has a viscosity, measured at 20° C., in the range of 150 to 2000 mPa·s, particularly preferably in the range of 150 to 1500 mPa·s, and especially in the range of 150 to 1000 mPa·s.

In addition, the present invention relates to a method for producing a hardener as described in the preceding, wherein the amine with one or more amino group of formula (I) is obtained by reductive alkylation of at least one primary amine with one or more carbonyl compounds of formula (III).

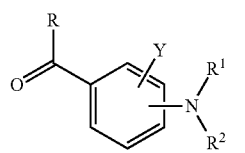

(III)

In formula (III), R, $R^1$, $R^2$ and Y have the meanings mentioned above.

Suitable carbonyl compounds of formula (III) are aldehydes, especially 4-dimethyl¬amino¬benzaldehyde, 4-dimethylamino-2-methyl-benzaldehyde, 4-dimethylamino-2-methoxy-benzaldehyde, 4-diethylaminobenzaldehyde, 4-dibutylaminobenzaldehyde, 4-(N-pyrrolidino)-benzaldehyde, 4-(N-piperidino)-benzaldehyde, 3-dimethyl¬amino¬benzaldehyde, 2-dimethyl¬amino¬benzaldehyde, and other ketones, especially 4'-dimethylaminoacetophenone, 4'-diethyl-aminoacetophenone, 4'-(N-pyrrolidino)-acetophenone, 4'-(N-piperidino)-acetophenone and 4-dimethylaminobenzophenone.

Preferred are 4-dimethyl¬amino¬benzaldehyde, 4-diethylaminobenzaldehyde, 4-dibutylaminobenzaldehyde, 4'-dimethylaminoacetophenone and 4-dimethylaminobenzophenone.

Most highly preferred is 4-dimethyl¬amino¬benzaldehyde, which is particularly readily available in industrial grade and has low toxicity.

A primary amine can also be reductively alkylated with a mixture of one or more carbonyl compounds of formula (III) and one or more additional carbonyl compounds, especially with a mixture containing benzaldehyde and/or salicylaldehyde.

The carbonyl compound is preferably used stoichiometrically relative to the primary amino groups, wherein amines with one or more amino groups of formula (I) free from primary amino groups are obtained.

The reductive alkylation is suitably performed in the presence of hydrogen and under elevated pressure. It can be performed directly with molecular hydrogen or indirectly by hydrogen transfer from other reagents. Preferably molecular hydrogen is used. The conditions are advantageously selected such that on one hand the primary amino groups to be reacted are reductively alkylated as completely as possible, and on the other hand, insofar as possible, no other constituents of amine and the carbonyl compound are hydrogenated or decomposed insofar as possible. The reaction is preferably performed at a hydrogen pressure of 5 to 100 bar, a temperature of 40 to 120° C. and in the presence of a suitable catalyst. Preferred catalysts are palladium on carbon (Pd/C), platinum on carbon (Pt/C), Adams catalyst and Raney Nickel, especially palladium on carbon and platinum on carbon.

An amine of formula (II) can be obtained particularly advantageously by the reductive alkylation of an amine of formula (IV) with one or more carbonyl compounds of formula (III).

In formula (IV) A and a have the aforementioned meanings.

Suitable amines of formula (IV) in a first embodiment are primary aliphatic polyamines, which are known as hardeners for epoxy resins, especially the following:

aliphatic, cycloaliphatic or arylaliphatic primary diamines, especially ethylenediamine, 1,2-propanediamine, 1,3-propanediamine 2-methyl-1,2-propanediamine 2,2-dimethyl-1,3-propanediamine 1,3-butanediamine 1,4-butanediamine 1,3-pentanediamine (DAMP), 1,5-pentanediamine, 1,5-diamino-2-methylpentane (MPMD), 2-butyl-2-ethyl-1,5-pentanediamine (C11-neodiamine), 1,6-hexanediamine, 2,5-dimethyl-1,6-hexanediamine, 2,2,4- and 2,4,4-trimethyl-hexamethylendiamine (TMD), 1,7-heptanediamine, 1,8-octanediamine, 1,9-nonanediamine, 1,10-decanediamine, 1,11-undecanediamine, 1,12-dodecanediamine, 1,2-, 1,3- and 1,4-diaminocyclohexane, bis-(4-aminocyclohexyl)-methane, bis-(4-amino-3-methylcyclohexyl)-methane, bis-(4-amino-3-ethylcyclohexyl)-methane, bis-(4-amino-3,5-dimethylcyclohexyl)-methane, bis-(4-amino-3-ethyl-5-methylcyclohexyl)-methane (M-MECA), 1-amino-3-aminomethyl-3,5,5-trimethyl-cyclohexane (=isophorone diamine or IPDA), 2- and 4-methyl-1,3-diaminocyclohexane and mixtures thereof, 1,3- and 1,4-bis-(aminomethyl)cyclohexane, 2,5(2,6)-bis-(aminomethyl)-bicyclo[2.2.1]heptane (NBDA), 3(4), 8(9)-bis-(aminomethyl)-tricyclo [5.2.1.0$^{2,6}$]decane, 1,4-diamino-2,2,6-trimethylcyclohexane (TMCDA), 1,8-menthanediamine, 3,9-bis-(3-aminopropyl)-2,4,8,10-tetraoxaspiro[5.5]undecane, 1,3-bis-(aminomethyl)benzene and 1,4-bis-(aminomethyl)benzene;

aliphatic, cycloaliphatic or arylaliphatic primary triamines such as 4-aminomethyl-1,8-octanediamine, 1,3,5-tris-(aminomethyl)benzene and 1,3,5-tris-(aminomethyl) cyclohexane;

Ether group-containing aliphatic primary diamines, especially bis-(2-aminoethyl)-ether, 3,6-dioxaoctane-1,8-diamine, 4,7-dioxadecane-1,10-diamine, 4,7-dioxadecane-2,9-diamine, 4,9-dioxadodecane-1,12-diamine, 5,8-dioxadodecane-3,10-diamine, 4,7,10-trioxamidecane-1,13-diamine and higher oligomers of these diamines, bis-(3-aminopropyl)polytetrahydrofurans and other polytetrahydrofuran-diamines, as well as polyoxyalkylene-diamines. The latter are typically products of the amination of polyoxyalkylenediols and are for example available under the name of Jeffamine® (from Huntsman), under the name of polyether amines (from BASF) or under the name of PC Amine® (from Nitroil). Especially suitable polyoxyalkylene diamines are Jeffamine® D-230, Jeffamine® D-400, Jeffamine® D-2000, Jeffamine® D-4000, Jeffamine® XTJ-511, Jeffamine® ED-600, Jeffamine® ED-900, Jeffamine® ED-2003, Jeffamine® XTJ-568, Jeffamine® XTJ-569, Jeffamine® XTJ-523, Jeffamine® XTJ-536, Jeffamine® XTJ-542, Jeffamine® XTJ-559, Jeffamine® EDR-104, Jeffamine® EDR-148, Jeffamine® EDR-176; polyether amine D 230, polyether amine D 400 and polyether amine D 2000, PC Amine® DA 250, PC Amine® DA 400, PC Amine® DA 650 and PC Amine® DA 2000;

primary polyoxyalkylene triamines, which are typically products of the amination of polyoxyalkylene triols and are available for example under the name of Jeffamine® (from Huntsman), under the name of polyether amines (from BASF) or under the name of PC Amine® (from Nitroil), such as especially Jeffamine® T-403, Jeffamine® T-3000, Jeffamine® T-5000, polyether amine T 403, polyether amine T 5000 and PC Amine® TA 403;

tertiary amino group-containing polyamines with two primary aliphatic amino groups, such as especially N,N'-bis-(aminopropyl)piperazine, N,N-bis-(3-aminopropyl)methylamine, N,N-bis-(3-aminopropyl)ethylamine, N,N-bis-(3-aminopropyl)propylamine, N,N-bis-(3-aminopropyl)cyclohexylamine, N,N-bis-(3-aminopropyl)-2-ethyl-hexylamine, as well as the products of the double cyanoethylation and subsequent reduction of fatty amines derived from natural fatty acids, such as N,N-bis-(3-aminopropyl)-dodecylamine and N,N-bis-(3-aminopropyl)-tallow alkylamines, available as Triameen® Y12D and Triameen® YT (from Akzo Nobel);

tertiary amino group-containing polyamines with three primary aliphatic amino groups, such as especially tris-(2-aminoethyl)amine, tris-(2-aminopropyl)amine and tris-(3-aminopropyl)amine;

secondary amino group-containing polyamines with two primary aliphatic amino groups, such as especially 3-(2-aminoethyl)aminopropylamine, bis-hexamethylenetriamine (BHMT), diethylenetriamine (DETA), triethylenetetramine (TETA), tetraethylenepentamine (TEPA), pentaethylenehexamine (PEHA) and higher homologs of linear polyethyleneamines such as polyethylenepolyamine with 5 to 7 ethyleneamine units (so-called "higher ethylenepolyamines," HEPA), products of the cyanoethylation or cyanobutylation and subsequent hydrogenation von primary di- and polyamines with at least two primary amino groups, such as dipropylenetriamine (DPTA), N-(2-aminoethyl)-1,3-propanediamine (N3-amine), N,N'-Bis(3-aminopropyl)ethylenediamine (N4-amine), N,N'-bis-(3-aminopropyl)-1,4-diaminobutane, N5-(3-aminopropyl)-2-methyl-1,5-pentanediamine, N3-(3-aminopentyl)-1,3-pentanediannine, N5-(3-amino-1-ethylpropyl)-2-methyl-1,5-pentanediamine and N,N'-bis-(3-amino-1-ethylpropyl)-2-methyl-1,5-pentanediamine.

Suitable amines of formula (IV) in an additional embodiment are amines with only one primary aliphatic amino group, especially the following:

monoamines, such as especially benzylamine, cyclohexylamine, 2-phenylethylamine, 2-methoxyphenylethylamine, 4-methoxyphenylethylamine, 3,4-dimethoxyphenylethylamine (homoveratrylamine), methylamine, ethylamine, propylamine, isopropylamine, 1- and 2-butylamine, isobutylamine, tert.-butylamine, 3-methyl-2-butylamine, 1-hexylamine, 1-octylamine, 2-ethyl-1-hexylamine, 2-methoxy-1-ethylamine, 2-ethoxy-1-ethylamine, 3-methoxy-1-propylamine, 3-ethoxy-1-propylamine, 3-(2-ethylhexyloxy)propylamine, 3-(2-methoxyethoxy)propylamine;

primary and secondary amino group-containing polyamines, such as especially N-methyl-1,2-ethanediamine, N-ethyl-1,2-ethanediamine, N-butyl-1,2-ethanediamine, N-hexyl-1,2-ethanediamine, N-(2-ethylhexyl)-1,2-ethanediamine, N-cyclohexyl-1,2-ethanediamine, 4-aminomethyl-piperidine, N-(2-aminoethyl)piperazine, N-methyl-1,3-propanediamine, N-butyl-1,3-propanediamine, N-(2-ethylhexyl)-1,3-propanediamine, N-cyclohexyl-1,3-propanediamine, 3-methylamino-1-pentylamine, 3-ethylamino-1-pentylamine, 3-cyclohexylamino-1-pentylamine, fatty diamines such as N-cocoalkyl-1,3-propanediamine and products of the Michael-type addition reaction of primary aliphatic diamines with acrylonitrile, maleic or fumaric acid diesters, citraconic acid diesters, acrylic and methacrylic acid esters, acrylic and methacrylic acid amides and itaconic acid diesters, reacted in a 1:1 molar ratio;

primary and tertiary amino group-containing polyamines, such as especially 3-(dimethylamino)-1-propylamine;

amino alcohols, such as especially 3-amino-1-propanol, 2-amino-1-butanol, 6-amino-1-hexanol, aminopropyl diethanolamine (APDEA), 4-(2-aminoethyl)-2-hydroxyethylbenzene, 3-aminomethyl-3,5,5-trimethylcyclohexanol, 2-(2-aminoethoxy)ethanol, 2-(2-(2-aminoethoxy)ethoxy)ethanol, 3-(2-hydroxy-ethoxy)propylamine and 3-(2-(2-hydroxyethoxy)-ethoxy)propylamine;

aminomercaptans, such as especially 2-aminoethanethiol (cysteamine), 3-aminopropanethiol, 4-amino-1-butanethiol and 6-amino-1-hexanethiol.

Preferred amines of formula (IV) are amines with a molecular weight of up to 500 g/mol, which optionally contain ether groups.

Particularly preferred is the amine of formula (IV) selected from the group consisting of MPMD, C11-neodiamine, 1,6-hexanediamine, 2,5-dimethyl-1,6-hexanediamine, TMD, 1,12-dodecanediamine, 1,4-diaminocyclohexane, bis-(4-aminocyclohexyl)methane, bis-(4-amino-3-methylcyclohexyl)methane, isophorone diamine, 1,3-bis-(aminomethyl)cyclohexane, NBDA, 3(4),8(9)-bis-(aminomethyl)-tricyclo[5.2.1.0$^{2,6}$]decane, 1,3-bis-(aminomethyl)benzene, BHMT, DETA, TETA, TEPA, PEHA, HEPA, DPTA, N3-amine, N4-amine, polyoxyalkylene diamines and polyoxyalkylene triamines with a molecular weight of 200 to 500 g/mol, especially the commercial types Jeffamine® D-230, Jeffamine® D-400 and Jeffamine® T-403 (from Huntsman).

The production of amines with one or more amino groups of formula (I) by reductive alkylation in the manner described is particularly advantageous for use as hardeners for epoxy resins, since primary amino groups are alkylated highly selectively, while secondary amino groups are scarcely alkylated further. The products of the preparation described can therefore be used after the reductive alkylation, without further processing, for hardening of epoxy resins in the manner described.

Amines with one or more amino groups of formula (I) may also be obtained in other ways than by reductive alkylation, especially by reacting primary amines with the corresponding chlorides or bromides in a suitable ratio. However, reaction mixtures are formed in this process, which typically contain a considerable fraction of double-alkylated amino groups.

An additional object of the invention is the use of the hardeners described for hardening at least one epoxy resin. For this purpose, the hardener is mixed with the epoxy resin in a suitable manner.

The hardener described has particularly advantageous properties. It has low volatility and low odor and has such a low reactivity toward $CO_2$ that—in contrast to many hardeners known from the prior art—when exposed to air it has no tendency to form crusts, precipitate, or increase in viscosity. The hardener is compatible with the usual commercial epoxy resins and can be combined with them and hardens surprisingly fast at ambient temperature, forming fully hardened compositions of high hardness and stability without undesirable blushing effects and with a surprisingly low tendency toward discoloration. The low tendency toward discoloration is an important prerequisite especially for applications in which the product remains visible over the long term, for example as a floor covering. Also particularly advantageous is the low viscosity of the hardeners. They are also usable in self-leveling coatings without non-incorporable diluents and consequently are highly suitable for low-emission systems.

The hardeners described, in addition to the amine with one or more amino groups of formula (I), may contain additional compounds suitable for hardening of epoxy resins, especially the following:

the previously described amines of formula (IV);
secondary aliphatic polyamines, such as especially the products of the reductive alkylation of the above-described amines of formula (IV) with other carbonyl compounds, especially with benzaldehyde and/or salicylaldehyde and/or 3-nitrobenzaldehyde and/or 3-pyridinecarbaldehyde; also N,N'-dibutyl-ethylenediamine, N,N'-di-tert.butyl-ethylenediamine, N,N'-diethyl-1,6-hexanediamine, 1-(1-methylethyl-amino)-3-(1-methylethyl-aminomethyl)-3,5,5-trimethylcyclohexane (Jefflink® 754 from Huntsman), N4-cyclohexyl-2-methyl-N2-(2-methylpropyl)-2,4-pentanediamine, N,N'-dialkyl-1,3-bis-(aminomethyl)benzene, especially N,N'-dibenzyl-1,3-bis-(aminomethyl)benzene, bis-(4-(N-3-butylamino)-cyclohexyl)-methane (Clearlink® 1000 from UOP), dialkylated DETA or TETA or TEPA or PEHA or N3- or N4-amine, especially the dibenzylated, optionally phenol group-containing types, furthermore styrenated polyamines such as styrenated 1,3-bis-(aminomethyl)benzene, commercially available as Gaskamine® 240 (from Mitsubishi Gas Chemical), N-alkylated polyether amines, for example the Jeffamine®-types SD-231, SD-401, ST-404 and SD-2001 (from Huntsman), as well as products of the Michael-type addition reaction of primary aliphatic polyamines with Michael acceptors such as maleic acid diesters, fumaric acid diesters, citraconic acid diesters, acrylic acid esters, methacrylic acid esters, cinnamic acid esters, itaconic acid diesters, vinylphosphonic acid diesters, vinylsulfonic acid aryl esters, vinylsulfones, vinylnitriles, nitroalkylenes or Knoevenagel condensation products such as those from malonic acid diesters and aldehydes such as formaldehyde, acetaldehyde or benzaldehyde;

aromatic polyamines, such as especially m- and p-phenylenediamine, 4,4'-, 2,4'- and 2,2'-diaminodiphenylmethane, 3,3'-dichloro-4,4'-diaminodiphenylmethane (MOCA), 2,4- and 2,6-toluoylenediamine, mixtures von 3,5-dimethylthio-2,4- and -2,6-toluoylenediamine (available as Ethacure® 300 from Albemarle), mixtures of 3,5-diethyl-2,4- and -2,6-toluoylenediamine (DETDA), 3,3',5,5'-tetraethyl-4,4'-diaminodiphenylmethane (M-DEA), 3,3',5,5'-tetraethyl-2,2'-dichloro-4,4'-diaminodiphenylmethane (M-CDEA), 3,3'-diisopropyl-5,5'-dimethyl-4,4'-diaminodiphenylmethane (M-MIPA), 3,3',5,5'-tetraisopropyl-4,4'-diaminodiphenylmethane (M-DIPA), 4,4'-diaminodiphenylsulfone (DDS), 4-amino-N-(4-aminophenyl)benzene sulfonamide, 5,5'-methylenedianthranilic acid, dimethyl-5,5'-methylene-dianthranilate, 1,3-propylene-bis-(4-aminobenzoate), 1,4-butylene-bis-(4-aminobenzoate), polytetramethylene oxide-bis-(4-aminobenzoate) (available as Versalink® from Air Products), 1,2-bis-(2-aminophenylthio)ethane, 2-methylpropyl-(4-chloro-3,5-diaminobenzoate) and tert.butyl-(4-chloro-3,5-diaminobenzoate);

amine/epoxide adducts, especially adducts of the amines mentioned with diepoxides in a molar ratio of at least 2/1, especially in a molar ratio of 2/1 to 6/1, or with monoepoxides in a molar ratio of at least 1/1, as well as reaction products of amines and epichlorohydrin, especially those of 1,3-bis-(aminomethyl)benzene, commercially available as Gaskamine® 328 (from Mitsubishi Gas Chemical);

polyamidoamines, which are reaction products of monovalent or polyvalent carboxylic acids or the esters or anhydrides thereof, especially a dimer fatty acid, and an aliphatic, cycloaliphatic or aromatic polyamine, especially a polyalkyleneamine such as DETA or TETA, used in a stoichiometric excess, especially the commercially available polyamidoamines Versamid® 100, 125, 140 and 150 (from Cognis), Aradur® 223, 250 and 848 (from Huntsman), Euretek® 3607 and 530 (from Huntsman) and Beckopox® EH 651, EH 654, EH 655, EH 661 and EH 663 (from Cytec); and Mannich bases, some of which are also called phenalkamines, which are reaction products of a Mannich reaction of phenols, especially cardanol, nonylphenol or tert.butylphenol, with aldehydes, especially formaldehyde, and polyamines, especially the commercially available Mannich bases Cardolite® NC-541, NC-557, NC-558, NC-566, Lite 2001 and Lite 2002 (from Cardolite), Aradur® 3440, 3441, 3442 and 3460 (from Huntsman), Accelerator 2950 (from Huntsman) and Beckopox® EH 614, EH 621, EH 624, EH 628 and EH 629 (from Cytec);

liquid mercaptan-terminated polysulfide polymers, known under the trade name of Thiokol® (from Morton Thiokol; for example available from SPI Supplies, or from Toray Fine Chemicals), especially the types LP-3, LP-33, LP-980, LP-23, LP-55, LP-56, LP-12, LP-31, LP-32 and LP-2; and also known under the trade name of Thioplast® (from Akzo Nobel), especially the types G 10, G 112, G 131, G 1, G 12, G 21, G 22, G 44 and G 4;

mercaptan-terminated polyoxyalkylene ethers, which can be obtained for example by reacting polyoxyalkylene di- and -triols either with epichlorohydrin or with an alkylene oxide, followed by sodium hydrogen sulfide;

mercaptan-terminated compounds in the form of polyoxyalkylene derivatives, known under the trade name of Capcure® (from Cognis), especially the types WR-8, LOF and 3-800;

polyesters of thiocarboxylic acids, for example pentaerythritol tetramercaptoacetate, trimethylolpropanetrimercaptoacetate, glycoldimercaptoacetate, pentaerythritoltetra-(3-mercaptopropionate), trimethylolpropanetri-(3-mercaptopropionate) and glycoldi-(3-mercaptopropionate), as well as the esterification products of polyoxyalkylenediols and -triols, ethoxylated trimethylolpropane and polyester diols with thiocarboxylic acids such as thioglycolic acid and 2- or 3-mercaptopropionic acid;

additional mercapto group-containing compounds, such as especially 2,4,6-trimercapto-1,3,5-triazine, 2,2'-(ethylenedioxy)diethanethiol (triethylene glycol dimercaptan) and ethanedithiol.

Preferred are DAMP, MPMD, C11-neodiamine, 1,6-hexanediamine, 2,5-dimethyl-1,6-hexanediamine, TMD, 1,12-dodecanediamine, 1,4-diaminocyclohexane, bis-(4-aminocyclohexyl)methane, bis-(4-amino-3-methylcyclohexyl)methane, IPDA, 3(4),8(9)-bis-(aminomethyl)-tricyclo[5.2.1.0$^{2,6}$]decane, 1,3-bis-(aminomethyl)benzene, N,N'-dibenzyl-1,3-bis-(aminomethyl)benzene, 1,3-bis-(aminomethyl)cyclohexane, Gaskamine® 240, NBDA, dibenzylated DETA, dibenzylated TETA, dibenzylated N3-amine and dibenzylated N4-amine, wherein these dibenzylated amines optionally contain phenol groups, polyoxyalkylene diamines and triamines with a molecular weight in the range of 200 to 500 g/mol, especially the types Jeffamine® D-230, Jeffamine® D-400 and Jeffamine® T-403, and also amine/epoxide adducts, especially Gaskamine® 328, as well as Mannich bases.

The hardeners according to the invention can also contain at least one accelerator. Also suitable as accelerators are substances which accelerate the reaction between amino groups and epoxy groups, especially acids or compounds hydrolyzable to acids, especially organic carboxylic acids such as acetic acid, benzoic acid, salicylic acid, 2-nitrobenzoic acid, lactic acid, organic sulfoxylic acids such as methanesulfonic acid, p-toluenesulfonic acid or 4-dodecylbenzenesulfonic acid, sulfonic acid esters, other organic or inorganic acids such as especially phosphoric acid, or mixtures of the aforementioned acids and acid esters; also tertiary amines such as especially 1,4-diazabicyclo[2.2.2]octane, benzyldimethylamine, □-methylbenzyldimethylamine, triethanolamine, dimethyl-aminopropylamine, imidazoles such as especially N-methylimidazole, N-vinylimidazole or 1,2-dimethylimidazole, salts of such tertiary amines, quaternary ammonium salts, such as especially benzyltrimethylammoniumchloride, amidines such as especially 1,8-diazabicyclo[5.4.0]undec-7-ene, guanidines such as especially 1,1,3,3-tetramethylguanidine, phenols, especially bisphenols, phenol resins and Mannich bases such as especially 2-(dimethylaminomethyl)phenol, 2,4,6-tris-(dimethylaminomethyl)phenol and polymers of phenol, formaldehyde and N,N-dimethyl-1,3-propanediamine, phosphites such as especially di- and triphenylphosphites, as well as mercapto group-containing compounds, such as those mentioned in the preceding.

Preferred accelerators are salicylic acid and 2,4,6-tris-(dimethylaminomethyl)-phenol.

The hardeners according to the invention can also contain at least one non-incorporable diluent, such as especially xylene, 2-methoxyethanol, dimethoxyethanol, 2-ethoxyethanol, 2-propoxyethanol, 2-isopropoxyethanol, 2-butoxyethanol, 2-phenoxyethanol, 2-benzyloxyethanol, benzyl alcohol, ethylene glycol, ethylene glycol dimethyl ether, ethylene glycol diethyl ether, ethylene glycoldibutyl ether, ethylene glycol diphenyl ether, diethylene glycol, diethylene glycol monomethyl ether, diethylene glycol monoethyl ether, diethylene glycol mono-n-butyl ether, diethylene glycol dimethyl ether, diethylene glycol diethyl ether, diethylene glycoldi-n-butylyl ether, propylene glycol butylether, propylene glycol phenyl ether, dipropylene glycol, dipropylene glycol monomethyl ether, dipropylene glycol dimethyl ether, dipropylene glycoldi-n-butyl ether, N-methylpyrrolidone, diphenylmethane, diisopropylnaphthalene, petroleum fractions such as Solvesso®-types (from Exxon), alkylphenols such as tert.butylphenol, nonylphenol, dodecylphenol and 8,11,14-pentadecatrienylphenol (cardanol, from cashew shell oil, which can be obtained for example as Cardolite NC-700 from Cardolite Corp., USA), styrenated phenol, bisphenols, aromatic hydrocarbon resins, especially phenol group-containing types, adipates, sebacates, phthalates, benzoates, organic phosphoric and sulfonic acid esters and sulfonamides. Preferred are benzyl alcohol, dodecylphenol, tert.butylphenol, styrenated phenol and phenol group-containing aromatic hydrocarbon resins, especially the Novares®-types LS 500, LX 200, LA 300 and LA 700 (from Rutgers).

Preferably the hardener contains very little or no non-incorporable diluents, particularly preferably less than 25% by weight, especially less than 15% by weight and most preferably less than 5% by weight. Especially no non-incorporable diluents are added to the hardeners.

An additional object of the invention is an epoxy resin composition containing at least one epoxy resin and at least one hardener as described in the preceding.

The usual industrial epoxy resins are suitable as epoxy resins. These are obtained in known ways, for example from oxidation of the corresponding olefins or from the reaction of epichlorohydrin with the corresponding polyols, polyphenols or amines.

Particularly suitable epoxy resins are so-called polyepoxide liquid resins, called "liquid resin" in the following. These have a glass transition temperature of less than 25° C., in contrast to the so-called solid resins, which have a glass transition temperature of more than 25° C. and can be ground into free-flowing powders at 25° C.

In one embodiment, the liquid resin is an aromatic polyepoxide. Suitable for this are, for example, liquid resins of formula (V),

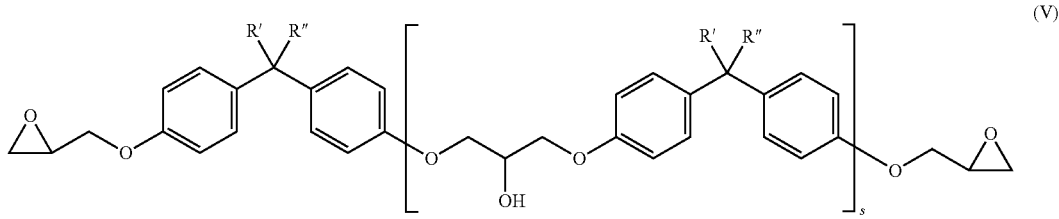

wherein R' and R" each independently of one another represents a hydrogen atom or a methyl group, and s on average represents a value of 0 to 1. Preferred are liquid resins of formula (V) in which the subscript s on average represents a value of less than 0.2.

The liquid resins of formula (V) are diglycidyl ethers of bisphenol A, bisphenol F and bisphenol A/F, wherein A stands for acetone and F for formaldehyde, which serve as educts for producing these bisphenols. In the case of bisphenol F, positional isomers may also exist, especially derived from 2,4'- and 2,2'-hydroxyphenylmethane.

Additional suitable aromatic liquid resins are the glycidylation products of dihydroxybenzene derivatives such as resorcinol, hydroquinone and pyrocatechol;

additional bisphenols or polyphenols such as bis-(4-hydroxy-3-methylphenyl)-methane, 2,2-bis-(4-hydroxy-3-methylphenyl)-propane (bisphenol C), bis-(3,5-dimethyl-4-hydroxyphenyl)-methane, 2,2-bis-(3,5-dimethyl-4-hydroxyphenyl)-propane, 2,2-bis-(3,5-dibromo-4-hydroxyphenyl)-propane, 2,2-bis-(4-hydroxy-3-tert.-butylphenyl)-propane, 2,2-bis-(4-hydroxyphenyl)-butane (bisphenol B), 3,3-bis-(4-hydroxyphenyl)-pentane, 3,4-bis-(4-hydroxyphenyl)-hexane, 4,4-bis-(4-hydroxyphenyl)-heptane, 2,4-bis-(4-hydroxyphenyl)-2-methylbutane, 2,4-bis-(3,5-dimethyl-4-hydroxyphenyl)-2-methylbutane, 1,1-bis-(4-hydroxyphenyl)-cyclohexane (bisphenol Z), 1,1-bis-(4-hydroxyphenyl)-3,3,5-trimethylcyclohexane (bisphenol TMC), 1,1-bis-(4-hydroxyphenyl)-1-phenylethane, 1,4-bis[2-(4-hydroxyphenyl)-2-propyl]benzene) (bisphenol P), 1,3-bis-[2-(4-hydroxyphenyl)-2-propyl]benzene) (bisphenol M), 4,4'-dihydroxydiphenyl (DOD), 4,4'-dihydroxybenzophenone, bis-(2-hydroxynaphth-1-yl)-methane, bis-(4-hydroxynaphth-1-yl)-methane 1,5-dihydroxy-naphthalene, tris-(4-hydro-xyphenyl) methane, 1,1,2,2-tetrakis-(4-hydroxyphenyl)ethane, bis-(4-hydroxy-phenyl)ether, bis-(4-hydroxyphenyl) sulfone;

condensation products of phenols with formaldehyde obtained under acidic conditions, such as phenol novolacs or cresol-novolacs, also called bisphenol F novolacs;

aromatic amines, such as aniline, toluidine, 4-aminophenol, 4,4'-methylenedi-phenyldiamine, 4,4'-methylenediphenyldi-(N-methyl)amine, 4,4'-[1,4-phenylene-bis-(1-methylethylidene)]bisaniline (bisanilin-P), 4,4'-[1,3-phenylene-bis-(1-methylethylidene)]-bisaniline (bisanilin M).

Also suitable as an epoxy resin is an aliphatic or cycloaliphatic polyepoxide, such as a glycidyl ether of a saturated or unsaturated, branched or unbranched, cyclic or open-chain $C_2$ to $C_{30}$ diol, such as ethylene glycol, propylene glycol, butylene glycol, hexanediol, octanediol, a polypropylene glycol, dimethylolcyclohexane, neopentylglycol or dibromo-neopentyl glycol;

a glycidyl ether of a tri- or tetrafunctional, saturated or unsaturated, branched or unbranched, cyclic or open-chain polyol such as castor oil, trimethylolpropane, trimethylolethane, pentaerythritol, sorbitol or glycerol, as well as alkoxylated glycerol or alkoxylated trimethylolpropane;

a hydrogenated bisphenol A, F or A/F liquid resin, or the glycidylation products of hydrogenated bisphenol A, F or A/F;

a N-glycidyl derivative of amides or heterocyclic nitrogen bases, such as triglycidyl cyanurate and triglycidyl isocyanurate, as well as reaction products von epichlorohydrin and hydantoin.

Additional possible epoxy resins are a bisphenol A, F or A/F solid resin of similar structure to the previously mentioned liquid resins of formula (V), but with instead the subscript s having a value of 2 to 12, and with a glass transition temperature of more than 25° C.

Finally, other suitable epoxy resins are epoxy resins from the oxidation of olefins, for example from the oxidation of vinylcylohexene, dicyclopentadiene, cyclo-hexadiene, cyclododecadiene, cyclododecatriene, isoprene, 1,5-hexadiene, butadiene, polybutadiene or divinylbenzene.

Preferred epoxy resins are liquid resins on the basis of a bisphenol, especially on der basis von bisphenol A, bisphenol F or bisphenol A/F, such as those available commercially for example from Dow, Huntsman and Hexion. These liquid resins have a low viscosity for epoxy resins and in the fully hardened state, good properties as coatings. They can optionally be present in combination with Bisphenol A solid resin or bisphenol F novolac epoxy resin.

The epoxy resin can contain a reactive diluent, especially a reactive diluent having at least one epoxide group. Suitable reactive diluents are, for example, the glycidyl ethers of monovalent or polyvalent phenols and aliphatic or cycloaliphatic alcohols, such as especially the previously mentioned polyglycidyl ethers von diols or polyols, as well as also especially phenylglycidyl ether, cresylglycidyl ether, benzylglycidyl ether, p-n-butyl-phenylglycidyl ether, p-tert.butyl-phenylglycidyl ether, nonylphenylglycidyl ether, allylglycidyl ether, butylglycidyl ether, hexylglycidyl ether, 2-ethylhexylglycidyl ether, as well as glycidyl ethers von natural alcohols, such as $C_8$- to $C_{10}$-alkylglycidyl ethers or $C_{12}$- to $C_{14}$-alkylglycidyl ethers. The addition of a reactive diluents to the epoxy resin causes a reduction of the viscosity as well as—in the fully hardened state of the epoxy resin composition—reduction of the glass transition temperature and the mechanical values.

Optionally the epoxy resin composition may contain additional constituents, especially auxiliaries and additives usually used in epoxy resin compositions, for example the following:

solvents, diluents, film forming aids or extenders, such as especially the aforementioned non-incorporable diluents;

reactive diluents, especially epoxy group-containing reactive diluents such as were mentioned in the preceding, epoxidized soybean oil or linseed oil, acetoacetate group-containing compounds, especially acetoacetylated polyols, butyrolactone, carbonates, aldehydes, as well as isocyanate- and reactive group-containing silicones;

polymers, such as polyamides, polysulfides, polyvinylformal (PVF), poly-vinylbutyral (PVB), polyurethanes (PUR), polymers with carboxyl groups, polyamides, butadiene-acrylonitrile copolymers, styrene-acrylonitrile copolymers, butadiene-styrene copolymers, homopolymers or copolymers of unsaturated monomers, especially from the group comprising ethylene, propylene, butylene, isobutylene, isoprene, vinyl acetate and alkyl(meth)acrylates, especially chlorosulfonated polyethylenes and fluorine-containing polymers, sulfonamide-modified melamines and purified montan waxes;

inorganic and organic fillers, for example ground or precipitated calcium carbonates, optionally coated with fatty acids, especially stearates, barite (heavy spar), talc, silica flour, silica sand, iron mica, dolomite, wollastonite, kaolins, mica (potassium-aluminum silicate), molecular sieves, aluminum oxides, aluminum oxide, aluminum hydroxide, magnesium hydroxide, silica, cement, gypsum, fly ash, carbon black, graphite, powdered metals such as aluminum, copper, iron, zinc, silver or steel, PVC powders or hollow beads;

fibers, especially glass fibers, carbon fibers, metal fibers, ceramic fibers or plastic fibers such as polyamide fibers or polyethylene fibers;

pigments, especially titanium dioxide and iron oxide;

the aforementioned accelerators;

rheology modifiers, such as especially thickeners, for example phyllosilicates such as bentonite, derivatives of castor oil, hydrogenated castor oil, polyamides, polyurethanes, urea compounds, pyrogenic silicas, cellulose ethers and hydrophobically modified polyoxyethylenes;

adhesion promoters, for example organoalkoxysilanes such as aminosilanes, mercaptosilanes, epoxysilanes, vinylsilanes, (methyl)acrylsilanes, isocyanatosilanes, carbamatosilanes, alkylsilanes, S-(alkylcarbonyl)mercaptosilanes and aldiminosilanes, as well as oligomeric forms of these silanes, especially 3-glycidoxypropyltrimethoxysilane, 3-aminopropyltrimethoxysilans, N-(2-aminoethyl)-3-aminopropyl-trimethoxysilane, N-(2-aminoethyl)-N'-[3-(trimethoxysilyl)propyl]ethylenediamine, 3-mercaptopropyltrimethoxysilane, 3-isocyanatopropyltrimethoxysilane, 3-ureidopropyltrimethoxysilane, 3-chloropropyltrimethoxysilane, vinyltrimethoxysilane, or the corresponding organosilanes with ethoxy groups instead of the methoxy groups;

stabilizers against oxidation, heat, light and UV radiation;

flame-retardant substances, especially compounds such as aluminum hydroxide (Al(OH)$_3$; also called ATH for "aluminum trihydrate"), magnesium hydroxide (Mg(OH)$_2$; also called MDH for "magnesium dihydrate"), ammonium sulfate ((NH$_4$)$_2$SO$_4$), boric acid (B(OH)$_3$), zinc borate, zinc phosphate, melamine borate and melamine cyanurate; phosphorus-containing compounds such as ammonium phosphate ((NH$_4$)$_3$PO$_4$), ammonium polyphosphate, melamine phosphate, melamine pyrophosphate, triphenyl phosphate, diphenyl cresyl phosphate, tricresyl phosphate, triethyl phosphate, tris-(2-ethylhexyl)phosphate, trioctyl phosphate, mono-, bis- and tris-(isopropylphenyl)phosphate, resorcinol-bis(diphenylphosphate), resorcinol diphosphate oligomer, tetraphenylresorcinol diphosphite, ethylenediamine-diphosphate and bisphenol A-bis(diphenyl phosphate); halogen-containing compounds such as chloroalkyl phosphate, especially tris-(chloroethyl) phosphate, tris-(chloropropyl)phosphate and tris-(dichloroisopropyl)phosphate, polybrominated diphenyl ethers, especially decabromodiphenyl ether, polybrominated diphenyl oxide, tris-[3-bromo-2,2-bis(bromomethyl)propyl]phosphate, tetrabromo-bisphenol A, bis-(2,3-dibromopropylether) of bisphenol A, brominated epoxy resins, ethylene-bis(tetrabromophtalimide), ethylene-bis(dibromonorbornanedicarboximide), 1,2-bis-(tribromophenoxy)ethane, tris-(2,3-dibromopropyl)isocyanurate, tribromophenol, hexabromocyclododecane, bis-(hexachlorocyclopentadieno)cyclooctane and chloroparaffins; as well as combinations of a halogen-containing compound and antimony trioxide (Sb$_2$O$_3$) or antimony pentoxide (Sb$_2$O$_5$);

surface-active substances, especially wetting agents, leveling agents, deaerating agents and defoamers;

biocides, such as algicides, fungicides or fungal growth inhibiting substances.

The epoxy resin composition preferably contains additional auxiliaries and additives, especially wetting agents, leveling agents, defoamers, stabilizers, pigmentes and catalysts, especially salicylic acid or 2,4,6-tris-(dimethylaminomethyl)phenol.

The epoxy resin composition preferably contains no or only a small amount of non-incorporable diluents, particularly preferably less than 10% by weight, especially less than 5% by weight, most preferably less than 2% by weight.

In the epoxy resin composition, the ratio of the number of groups reactive toward epoxy groups to the number epoxy groups falls in the range of 0.5 to 1.5, preferably 0.7 to 1.2.

The amine hydrogens and optionally additional groups reactive toward epoxy groups present in the epoxy resin composition react with the epoxy groups by ring opening (addition reactions). As a result of this reaction, the composition polymerizes and ultimately hardens completely. It is known to persons skilled in the art that primary amino groups are difunctional with respect to epoxy groups and a primary amino group thus counts as two groups reactive toward epoxy groups.

In particular, the epoxy resin composition is a two-component composition, consisting of a resin component and a hardener component, wherein the epoxy resin is a constituent of the resin component and the hardener described is a constituent of the hardener component.

The components of the two-component composition are each stored in their own containers. Additional constituents of the two-component epoxy resin composition can be present as a constituent of the resin or the hardener component, wherein additional constituents reactive toward epoxy groups are preferably a constituent of the hardener component. A suitable container for storing the resin or the hardener component is especially a drum, a hobbock, a bag, a bucket, a canister, a cartridge or a tube. The components are storable, which means that they can be stored for several months to one year or longer before use without their respective properties changing to a degree relevant for their use. To use the two-component epoxy resin composition, the resin component and the hardener component are mixed together shortly before or during the application. The mixing ratio between the two components is preferably selected such that the groups of the hardener component reactive toward epoxy groups are present in a suitable ratio to the epoxy groups of the resin component, as described in the preceding. In parts by weight, the mixing ratio between the resin component and the hardener component is usually in the range of 1:10 to 10:1.

The mixing of the two component is performed using a suitable method; it may take place continuously or batchwise. If the mixing takes place before the application it is necessary to make sure that too much time does not elapse between the mixing of the components and the application, since this could lead to problems such as slow or incomplete development of the bond with the substrate. The mixing especially takes place at ambient temperature, which is typically in the range of about 5 to 50° C., preferably about 10 to 30° C.

With the mixing of the two components, the hardening by chemical reaction, as described in the preceding, begins. The hardening especially takes place at ambient temperature. It typically takes from several days to weeks before it is largely complete under the given conditions. The duration depends, among other things, on the temperature, the reactivity of the constituents and their stoichiometry as well as the presence of accelerators.

An additional object of the invention is thus a hardened composition obtained from the hardening of an epoxy resin composition as described in the document that follows.

The epoxy resin composition is applied to at least one Substrate, wherein the following are particularly suitable:
- glass, glass ceramics, concrete, mortar, brick, tile, hard plaster and natural stone such as granite or marble;
- metals and alloys, such as aluminum, iron, steel and non-ferrous metal, as well as coated metals and alloys, such as galvanized or chrome-plated metals;
- leather, textiles, paper, wood, wooden materials bonded with resins, for example phenol, melamine or epoxy resins, resin-textile-composite materials and additional so-called polymer composites;
- plastics, such as polyvinyl chloride (hard and soft PVC), acrylonitrile-butadiene-styrene-copolymers (ABS), polycarbonate (PC), polyamide (PA), polyester, poly(methyl methacrylate) (PMMA), polyester, epoxy resins, polyurethanes (PUR), polyoxymethylene (POM), polyolefins (PO), polyethylene (PE) or polypropylene (PP), ethylene/propylene copolymers (EPM) and ethylene/propylene/diene terpolymers (EPDM), wherein the plastics can preferably be surface-treated with plasma, corona or flame;
- fiber-reinforced plastics, such as Fiber-reinforced plastics, such as carbon fiber-reinforced plastics (CFRO), glass fiber-reinforced plastics (GFRP) and sheet molding compounds (SMC);
- coated substrates, such as powder-coated metals or alloy;
- paints and lacquers, especially automotive enamels.

If necessary, the substrates can be pretreated prior to application of the epoxy resin composition. Pretreatments of this type especially include physical and/or chemical cleaning processes, for example grinding, sand blasting, shot peening, brushing or the like, wherein dusts produced during the process are advantageously drawn off by suction, as well as treating with cleaners or solvents applying an adhesion promoter, an adhesion-promoting solution or a primer.

The epoxy resin composition described is advantageously usable as a fiber composite material (Composite), potting compound, sealant, adhesive, lining, coating, paint, lacquer, waterproofing compound, base coat or primer.

It can especially be used as a casting composition, sealant or adhesive, for example as a potting compound, waterproofing compound, auto body adhesive, sandwich element adhesive, half-shell adhesive, for example for rotor blades of wind power plants, bridge element adhesive or anchoring adhesive; as well as lining, coating, paint, lacquer, waterproofing compound, base coat or primer for construction and industrial applications, especially as floor covering and floor coating for interior rooms such as offices, factory buildings, gymnasia or cold storage rooms, or in the outdoor sector for balconies, terraces, parking levels, bridges or roofs, as protective coating for concrete, cement, metals, plastics or wood, for example for surface sealing of wooden constructions, vehicles, loading platforms, tanks, silos, shafts, conduits, pipelines, machinery or steel construction, for example of ships, piers, off-shore platforms, lock gates, hydro power plants, river structural works, swimming pools, wind power plants, bridged, chimneys, cranes or bulkheads, wherein these coatings protect the respective substrates especially from corrosion, abrasion, atmospheric humidity, water, and/or effects of salt or chemicals; and also as primer, bonding coat, anticorrosion primer or for water-repellent treatment of surfaces. The composition described is especially suitable as a coating for so-called heavy corrosion protection in and on the water, especially in and on seawater. In addition, an additional coating, an additional lining, or an additional coat of paint can also be applied to the completely or partially cured epoxy resin composition, especially when it is used as a coating, lining or paint, this additional layer can likewise involve an epoxy resin composition, but also another material, especially a polyurethane or polyurea coating.

The epoxy resin composition described is usable with particular advantage as a coating. Coatings include all types of coatings applied extending in or on a surface, especially also paints, lacquers, waterproof coatings, base coats and primers, as previously described. The epoxy resin composition described is especially advantageously usable in low-emission systems with eco quality labeling, for example according to Emicode (EC1 Plus), AgBB, DIBt, Der Blaue Engel [The Blue Angel], AFSSET, RTS (M1) and US Green Building Council (LEED), as well as for coatings that are supposed to be resistant to mechanical stress, atmospheric humidity, effects of water and/or salt, excreta, chemicals or foodstuffs.

As a coating, the epoxy resin composition is advantageously used in a coating method in which it has a liquid consistency with low viscosity and good leveling properties and can especially be applied as a self-leveling coating on basically flat surfaces or as paint. Preferably the epoxy resin composition in this application immediately after the resin and hardener components are mixed has a viscosity, measured at 20° C., in the range of 300 to 2'000 mPa·s, preferably in the range of 300 to 1'500 mPa·s, especially in the range of 300 to 1'000 mPa·s. Within the processing time the mixed composition is applied extending on a surface as a thin film with a layer thickness of typically 50 µm to about 5 mm on a substrate, typically at ambient temperature. The application is done, for example, by casting onto the substrate to be coated. In this process the composition in the liquid state is distributed uniformly with the aid of, for example, a doctor blade or a notched trowel. In addition, the uniformly distributed composition can be leveled and deaerated with a spiked roller. However, the application can also take place manually using a brush or roller or as a spray application, for example as an anti-corrosion coating on steel. During hardening, typically practically clear, lustrous and non-sticky films of high hardness and stability and a low tendency to discoloration, displaying good adhesion to a great variety of substrates, are formed. With the aid of the hardeners described, epoxy resin coatings are available, which even unfavorable reaction conditions, i.e., those that promote blushing, especially at low hardening temperatures in the range of 5 to 10° C. and high atmospheric humidity, harden completely to form high-quality films.

An additional object of the invention is an article containing a hardened composition obtained by the hardening of the epoxy resin composition described. The hardened composition in such cases exists particularly in the form of a coating.

The epoxy resin composition described is characterized by advantageous properties. It has only a slight odor and can be handled well even without additional diluents. It has a surprisingly low viscosity and hardens at ambient temperature surprisingly quickly and without objectionable blushing effects, especially also under cold, moist conditions. In the completely hardened state, it has high hardness and stability and a low tendency to discoloration.

EXAMPLES

In the following, exemplified embodiments are presented which are intended to explain the invention described in greater detail. Naturally, the invention is not limited to these exemplified embodiments described.

1. Description of the Measurement Methods

The amine content, in other words the total content of amino groups in the compounds produced, was determined titrimetrically (with 0.1N HClO$_4$ in glacial acetic acid against crystal violet) and is always stated in mmol N/g.

Infrared spectra (FT-IR) were measured as undiluted films on a FT-IR 1600 device from Perkin-Elmer, equipped with a horizontal ATR measurement unit with a ZnSe crystal; the absorption bands are given in wave numbers (cm$^{-1}$) (measurement windows: 4000-650 cm$^{-1}$).

The viscosity was measured on a thermostatically controlled Rheotec RC30 cone-plate viscometer (cone diameter 50 mm, cone angle 1°, cone tip-plate distance 0.05 mm, shear rate 10-100 s$^{-1}$).

2. Substances Used:

T ETA: Triethylenetetramine (technical grade, amine content about 25.7 mmol N/g)

N4-amine: N,N'-Bis(3-aminopropyl)ethylenediamine (from BASF)

Jeffamine® D-230: Polypropylene glycol diamine, mean molecular weight about 240 g/mol, amine content about 8.29 mmol N/g (from Huntsman)

Jeffamine® T-403: Polypropylene glycol triamine, mean molecular weight about 460 g/mol, amine content about 6.29 mmol N/g (from Huntsman)

Araldite® GY 250: Bisphenol A diglycidyl ether; epoxy equivalent about 187.5 g/Eq (from Huntsman)

Epikote® 862 Bisphenol F diglycidyl ether; epoxide equivalent weight about 169 g/Eq (from Hexion)

Araldite® DY-E: Monoglycidyl ether of a C$_{12}$- to C$_{14}$-Alkohol; epoxy equivalent about 290 g/Eq (from Huntsman)

Ancamine® K 54: 2,4,6-tris-(dimethylaminomethyl)phenol (from Air Products)

3. Production of Hardeners

General Manufacturing Instructions for Reductive Alkylation

In a round-bottom flask under a nitrogen atmosphere, the aldehyde and an amine were dissolved in a sufficient quantity of isopropanol. The solution was agitated for 30 minutes at room temperature and then hydrogenated at a hydrogen pressure of 80 bar, a temperature of 80° C. and a flow rate of 3 ml/min on a continuously operating hydrogenation apparatus with Pd/C-fixed bed catalyst. The reaction was monitored using IR spectroscopy to check whether the imine band at about 1665 cm$^{-1}$. Then the solution was concentrated under vacuum at 80° C.

Hardener H1: According to the general manufacturing instructions for reductive alkylation, 29.8 g of 4-dimethyl¬ amino¬ benzaldehyde and 18.4 g TETA were reacted. A clear, light yellowish oil with a viscosity of 750 mPa·s at 20° C. and an amine content of 14.00 mmol N/g was obtained.

FT-IR: 2881, 2801, 1613, 1524, 1442, 1340, 1222, 1161, 1127, 946, 800, 760.

Hardener H2: According to the general manufacturing instructions for reductive alkylation, 29.8 g 4-dimethyl¬ amino¬ benzaldehyde and 17.4 g N4-amine were reacted. A clear, light yellowish oil with a viscosity of 870 mPa·s at 20° C. and an amine content of 12.69 mmol N/g was obtained.

FT-IR: 2921, 2880, 2799, 1613, 1519, 1443, 1340, 1221, 1185, 1162, 1124, 1059, 946, 802, 749.

Hardener H3: According to the general manufacturing instructions for reductive alkylation, a mixture of 6.0 g 4-dimethyl¬ amino¬ benzaldehyde and 17.0 g benzaldehyde was reacted with 17.4 g N4-amine. A clear, light yellowish oil with a viscosity of 300 mPa·s at 20° C. and an amine content of 10.94 mmol N/g was obtained.

FT-IR: 2924, 2882, 2805, 1614, 1521, 1494, 1452, 1340, 1162, 1117, 1073, 1060, 1027, 946, 804, 730.

Hardener H4: According to the general manufacturing instructions for reductive alkylation, a mixture of 14.9 g 4-dimethyl¬ amino¬ benzaldehyde, 8.5 g benzaldehyde and 2.4 g salicylaldehyde was reacted with 17.4 g N4-amine. A clear, yellowish oil with a viscosity of 530 mPa·s at 20° C. and an amine content of 12.37 mmol N/g was obtained.

FT-IR: 2923, 2882, 2803, 1613, 1567, 1520, 1452, 1341, 1258, 1223, 1186, 1162, 1114, 1059, 1027, 946, 803, 750, 733, 698.

Hardener H5: According to the general manufacturing instructions for reductive alkylation, 29.8 g of 4-dimethyl¬ amino¬ benzaldehyde and 11.6 g of 1,5-diamino-2-methylpentane were reacted. A clear, yellowish oil with a viscosity of 570 mPa·s at 20° C. and an amine content of 10.15 mmol N/g was obtained.

FT-IR: 2921, 2870, 2846, 2798, 1613, 1567, 1519, 1475, 1442, 1340, 1223, 1183, 1162, 1127, 1110, 1059, 946, 801, 753.

Hardener H6: According to the general manufacturing instructions for reductive alkylation, 29.8 g 4-dimethyl¬ amino¬ benzaldehyde and 13.6 g 1,3-bis-(aminomethyl)benzene were reacted. A clear, light yellowish oil with a viscosity of 510 mPa·s at 20° C. and an amine content of 9.95 mmol N/g was obtained.

FT-IR: 2780, 1612, 1517, 1340, 1159, 945, 800.

Hardener H7: According to the general manufacturing instructions for reductive alkylation, 29.8 g 4-dimethyl¬ amino¬ benzaldehyde and 24.0 g Jeffamine® D-230 were reacted. A clear, light yellowish oil with a viscosity of 250 mPa·s at 20° C. and an amine content of 7.45 mmol N/g was obtained.

FT-IR: 2966, 2864, 2800, 1614, 1521, 1444, 1340, 1224, 1161, 1102, 1062, 946, 804.

Hardener H8: According to the general manufacturing instructions for reductive alkylation, 20.3 g 4-dimethyl¬ amino¬ benzaldehyde and 20.0 g Jeffamine® T-403 were reacted. A clear, light yellowish oil with a viscosity of 190 mPa·s at 20° C. and an amine content of 6.61 mmol N/g was obtained.

FT-IR: 2965, 2865, 1615, 1522, 1445, 1373, 1342, 1161, 1102, 947, 804.

Hardener HV1 (Comparison): According to the general manufacturing instructions for reductive alkylation, 17.2 g benzaldehyde and 15.0 g TETA were reacted. A clear, light yellowish oil was obtained with a viscosity of 260 mPa·s at 20° C. and an amine content of 13.10 mmol N/g was obtained.

Hardener HV2 (Comparison): According to the general manufacturing instructions for reductive alkylation, 21.2 g benzaldehyde and 11.6 g 1,5-diamino-2-methylpentane were reacted. A clear, light yellowish oil with a viscosity of 420 mPa·s at 20° C. and an amine content of 6.67 mmol N/g was obtained.

Hardener HV3 (Comparison): According to the general manufacturing instructions for reductive alkylation, 21.2 g benzaldehyde and 13.6 g 1,3-bis-(aminomethyl)benzene were reacted. A clear, light yellowish oil with a viscosity of 230 mPa·s at 20° C. and an amine content of 6.41 mmol N/g was obtained.

4. Preparation of Epoxy Resin Compositions

For each example, the constituents shown in Table 1 were in the indicated quantities (in parts by weight) using a centrifugal mixer (SpeedMixer™ DAC 150, FlackTek Inc.). 10 minutes after the mixing, in each case the viscosity of the compositions was determined at 20° C. ("viscosity (10')"). In addition, in each case a first film with a layer thickness of 500 µm was drawn on a glass plate and this was held or hardened at 23±1° C. and 50±5% relative humidity (=standard climate, abbreviated as "SC" in the following). The König hardness of these films (pendulum hardness according to König, measured according to DIN EN ISO 1522) was determined after 2 days ("König hardness (SC) (2 d)"), 4 days ("König hardness (SC) (4 d)"), 7 days ("König hardness (SC) (7 d)") and after 4 weeks ("König hardness (SC) (4 w)"). After 4 weeks, the appearance of the films was evaluated (designated in the table as "Appearance SC"). The designation "clean" was applied to a film that was clear and had a shiny, non-sticky surface without structure. The term "structure" means any type of marking or pattern on the surface. After an additional 4 weeks under SC, the color of the film was evaluated. In addition, in each case a second film with a layer thickness of 500 μm was drawn on a glass plate and this was stored immediately after application for 7 days at 8° C. and 80% relative humidity and then stored or hardened for 4 weeks in SC. Then the appearance of this film was evaluated (designated in the tables by "Appearance (8°/80%)," in the same way as for the Appearance (SC). Furthermore the König hardness was determined on the films hardened in this way, in each case after 7 days at 8° C. and 80% relative humidity ("König h. (8°/80%) (7 d cold)"), then after an additional 2 days under SC ("König h. (8°/80%) (+2 d SC)") or 7 days under SC ("König h. (8°/80%) (+7 d SC") or 4 weeks in SC ("König h. (8°/80%) (+4 w SC)").

The results are presented in Table 1.

The invention claimed is:
1. Method for hardening at least one epoxy resin, comprising: hardening the epoxy resin by reacting with a hardener, the hardener containing one or more amines with one or more amino groups of formula (I),

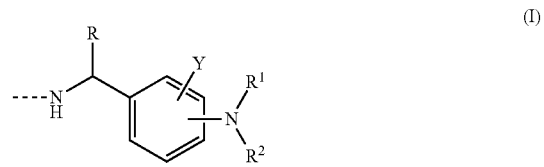

wherein
R represents a hydrogen atom or an alkyl group with 1 to 12 C atoms;
$R^1$ and $R^2$ each independently represent an alkyl or arylalkyl group with 1 to 12 C atoms, or together represent an alkylene group with 4 to 5 C atoms; and
Y represents a hydrogen atom or an alkyl or alkoxy group with 1 to 12 C atoms.

TABLE 1

Composition and properties of the compositions Z1 to Z11 and the comparison compositions ZV1 to ZV4.

| composition | Z1 | Z2 | ZV1 (Comp.) | ZV2 (Comp.) | Z3 | Z4 | Z5 |
|---|---|---|---|---|---|---|---|
| Araldite ® GY-250 | 111.0 | 111.0 | 111.0 | 111.0 | 167.2 | 167.2 | 167.2 |
| Epikote ® 862 | 50.2 | 50.2 | 50.2 | 50.2 | — | — | — |
| Araldite ® DY-E | 31.8 | 31.8 | 31.8 | 31.8 | 31.8 | 31.8 | 31.8 |
| Hardener (type, | H1, | H1, | HV1, | HV1, | H2, | H2, | H3, |
| quantity) | 103.2 | 103.2 | 81.6 | 81.6 | 110.2 | 110.2 | 91.5 |
| Ancamine ® K 54 | 5.9 | — | 5.5 | — | 6.2 | — | 5.8 |
| Viscosity (10') [Pa · s] | 0.85 | 0.97 | 0.45 | 0.55 | 1.50 | 1.53 | 0.86 |
| König hardness [s] | | | | | | | |
| (2 d) | 158 | 113 | 60 | 7 | 162 | 113 | 126 |
| (4 d) | 168 | 140 | 112 | 17 | 200 | 167 | 169 |
| (SC) (7 d) | 171 | 150 | 145 | 35 | 207 | 186 | 188 |
| (4 w) | 179 | 160 | 165 | 98 | 224 | 214 | 209 |
| Appearance (SC), | clean, | clean, | clean, | clean, | clean, | clean, | clean, |
| color | colorless | colorless | colorless | colorless | colorless | colorless | colorless |
| König h. [s] (7 d cold) | 95 | 67 | 21 | 6 | 88 | 63 | 66 |
| (+2 d SC) | 143 | 116 | 82 | 13 | 179 | 157 | 162 |
| (8°/80%) (+7 d SC) | 144 | 141 | 105 | 34 | 206 | 196 | 195 |
| (+4 w SC) | 158 | 153 | 168 | 85 | 213 | 207 | 200 |
| Appearance (8°/80%) | clean | clean | clean | clean | clean | clean | clean |

| Composition | Z6 | Z7 | Z8 | ZV3 (Comp.) | Z9 | Z10 | ZV4 (Comp.) |
|---|---|---|---|---|---|---|---|
| Araldite ® GY-250 | 167.2 | 167.2 | 167.2 | 167.2 | 167.2 | 167.2 | 167.2 |
| Araldite ® DY-E | 31.8 | 31.8 | 31.8 | 31.8 | 31.8 | 31.8 | 31.8 |
| hardener (type, | H3, | H4, | H5, | HV2, | H6, | H6, | HV3, |
| quantity) | 91.5 | 100.0 | 191.2 | 148.2 | 201.3 | 201.3 | 158.2 |
| Ancamine ® K 54 | — | — | 7.8 | 6.9 | 8.0 | — | 7.1 |
| viscosity (10') [Pa · s] | 0.84 | 1.29 | 0.73 | 0.33 | 0.94 | 1.00 | 0.34 |
| König hardness [s] | | | | | | | |
| (2 d) | 59 | 123 | 70 | 10 | 66 | 42 | 27 |
| (4 d) | 122 | 167 | 113 | 27 | 132 | 99 | 108 |
| (SC) (7 d) | 152 | 190 | 136 | 34 | 151 | 123 | 146 |
| (4 w) | 192 | 207 | 160 | 36 | 176 | 161 | 154 |
| Appearance (SC), | clean, | clean, | clean, | clean, | clean, | clean, | clean, |
| color | colorless | colorless | colorless | colorless | colorless | colorless | colorless |
| König h.[s] (7 d cold) | 35 | 63 | 24 | 10 | 49 | 34 | 6 |
| (+2 d SC) | 78 | 157 | 77 | 27 | 140 | 85 | 78 |
| (8°/80%) (+7 d SC) | 162 | 192 | 139 | 52 | 168 | 134 | 161 |
| (+4 w SC) | 185 | 213 | 158 | 53 | 176 | 147 | 169 |
| Appearance (8°/80%) | clean | clean | clean | clean | clean | clean | clean |

"Comp." stands for "Comparison";
"Königs." stands for "König hardness"

2. The method according to claim 1, wherein the amine with one or more amino groups of formula (I) contains one, two or three amino groups of formula (I).

3. The method according to claim 1, wherein R represents a hydrogen atom or a methyl group.

4. The method according to claim 1, wherein $R^1$ and $R^2$ each represents an alkyl group with 1 to 4 C atoms.

5. The method according to claim 1, wherein Y represents a hydrogen atom or a methyl group.

6. The method according to claim 1, wherein Y represents a hydrogen atom and $R^1$ and $R^2$ each represent a methyl group and the tertiary amino group is in para-position.

7. The method according to claim 1, wherein the amine with one or more amino groups of formula (I)
either is an amine of formula (II),

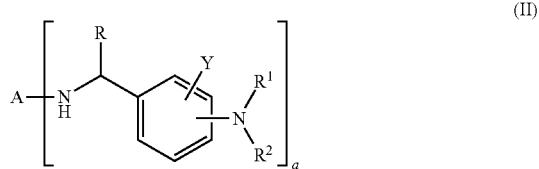

(II)

wherein
A represents an a-valent hydrocarbon radical with a molecular weight in the range of 28 to 5000 g/mol, which optionally contains ether groups, amino groups, hydroxyl groups or mercapto groups; and
a represents an integer from 1 to 3;
or an adduct of an amine of formula (II) with one or more compounds containing at least one reactive group selected from the group consisting of epoxide, episulfide, aziridine, cyclocarbonate, isocyanate, isothiocyanate, acrylate, methacrylate and acrylamide groups.

8. The method according to claim 7, wherein A either represents an a-valent alkyl, cycloalkyl- or arylalkyl radical with 2 to 20 C atoms or an a-valent polyalkyleneamine radical with 1 to 10 secondary amino groups or represents an a-valent polyoxyalkylene radical with 1 to 7 ether groups, wherein these radicals may have one or two primary or secondary aliphatic amino groups.

9. The method according to claim 7, wherein the adduct is an adduct of an amine of formula (II) with at least one mono- or polyepoxide.

10. The method according to claim 7, wherein the amine with one or more amino groups of formula (I) is an amine of formula (II).

11. Epoxy resin composition containing at least one epoxy resin and at least one hardener containing one or more amines with one or more amino groups of formula (I),

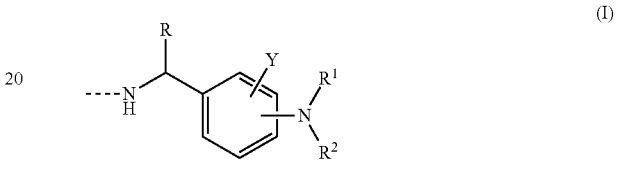

(I)

wherein
R represents a hydrogen atom or an alkyl group with 1 to 12 C atoms;
$R^1$ and $R^2$ each independently represent an alkyl or arylalkyl group with 1 to 12 C atoms, or together represent an alkylene group with 4 to 5 C atoms; and
Y represents a hydrogen atom or an alkyl or alkoxy group with 1 to 12 C atoms.

12. Hardened composition obtained from the hardening of the epoxy resin composition according to claim 11.

13. Article containing a hardened composition according to claim 12.

* * * * *